United States Patent [19]

Blackburn

[11] 4,456,522

[45] Jun. 26, 1984

[54] SUPPORT AND ANCHORING MECHANISM FOR MEMBRANES IN SELECTIVELY RESPONSIVE FIELD EFFECT DEVICES

[75] Inventor: Gary F. Blackburn, North Salt Lake, Utah

[73] Assignee: Critikon, Inc., Tampa, Fla.

[21] Appl. No.: 304,722

[22] Filed: Sep. 23, 1981

[51] Int. Cl.³ ............................................. G01N 27/46
[52] U.S. Cl. .................................... 204/416; 204/403; 204/418; 204/419; 357/25; 357/23.1; 427/82
[58] Field of Search ............... 204/416, 418, 419, 403; 427/82; 357/23 R, 23 MG, 25, 71

[56] References Cited

U.S. PATENT DOCUMENTS

| 3,410,778 | 11/1968 | Krasberg | 204/415 |
| 3,645,875 | 2/1972 | Record et al. | 204/429 |
| 4,020,830 | 5/1977 | Johnson et al. | 204/403 |
| 4,180,771 | 12/1979 | Guckel | 357/25 |
| 4,273,636 | 6/1981 | Shimada et al. | 357/25 |
| 4,302,530 | 11/1981 | Zemel | 427/82 |
| 4,305,802 | 12/1981 | Koshiishi | 204/418 |

Primary Examiner—T. Tung
Attorney, Agent, or Firm—Audley A. Ciamporcero, Jr.

[57] ABSTRACT

In the formation of a chemically sensitive field effect device, prior to formation of the gate membrane, an aluminum pad is disposed over the gate, and a polyimide layer is disposed thereover. Photoresist and etching steps produce openings in the polyimide to form a gridwork which is anchored to the device on the periphery of the gate. The aluminum layer is etched completely away, forming a void defined by the suspended polyimide mesh on one side, and the gate insulator on the other. Polymeric membrane is formed in the void by insertion in liquid form.

3 Claims, 5 Drawing Figures

SUPPORT AND ANCHORING MECHANISM FOR MEMBRANES IN SELECTIVELY RESPONSIVE FIELD EFFECT DEVICES

FIELD OF THE INVENTION

This invention relates to semiconductor devices whose electrical characteristics are dependent on the selective interaction of a portion thereof with specified substances, and more particularly to methods and apparatus whereby the selectively reactive region constitutes a membrane which is well-anchored in position thereover.

BACKGROUND OF THE INVENTION

There exists a class of devices exemplified by U.S. Pat. No. 4,020,830 to Johnson et al., dated May 3, 1977, entitled "SELECTIVE CHEMICAL SENSITIVE FET TRANSDUCERS", which features electrical characteristics modulated by the interaction of a chemically selective system to specified ambient materials. In accordance with the Johnson patent, a substrate layer carries respective drain and source regions, separated by a region or channel over which is disposed an insulating layer and a chemically selective system for specified interaction with predetermined ambient materials. The chemically selective system generally takes the form of a membrane which interacts with the materials, and modulates the drain to source electrical conduction based on concentrations of the specified ambient substances.

The Johnson et al. patent contemplates chemically selective systems for measuring various types of ambient conditions, including gas concentrations, ion activity, immunochemical concentrations, concentrations of enzymes and substrates, and the like, and indeed many such applications have found favor in a variety of disparate fields. While the nomenclature in the art has tended to designate these respective applications separately, for example utilizing the designation "CHEMFET" for chemically selective membrane devices, "ISFET" for ionically reactive devices, "IMMUNOFET" for immunologically reactive devices, and so forth, for purposes of this application the term "chemfet", or simply "device" shall be utilized generically to encompass all such apparatus, irrespective of the type of sensing or reaction utilized, character of the membrane employed, or nature of the ambient substance to be monitored. Likewise, the terms chemfet or device as used herein shall embrace transistor-type, diode-type, or the like other devices which feature similar conductivity modulation based on membrane-substance interaction.

In recent times, much effort has been expended in the development of device configurations and manufacturing processes which will facilitate large-scale production of reliable, stable, and well-calibrated devices. For example, device encapsulation, membrane formulation, and membrane disposition have proven to be formidable technical problems.

It is a general object of the present invention to provide device configurations and manufacturing processes for the production of superior chemfet devices, which have high reliability, well quantified specifications, suitable physical integrity, and a reasonable operational lifespan.

With particular reference to the membrane aspect of the devices, it is to be noted that problems have been encountered both in the fabrication phase, and in the use and lifespan aspects of the devices. For example, polymeric membranes with high plasticizer content have found favor in the field, but production yield, operational reproducability, and physical integrity have all too often characterized the devices. Obviously, a chemfet membrane which is inadequately adhered to the gate insuator at the time of production will result in, at best, a gradual detachment of the membrane from the surrounding encapsulation. This results not only in a progressive loss of chemical response, but sooner or later in total failure of the device.

Accordingly, more specific objects of the present invention relate to provision of mechanisms, systems, and techniques whereby chemfet membranes are reliably, certainly, and substantially permanently attached to the device, thereby achieving superior mechanical integrity, and improved, well characterized electrochemical operation.

SUMMARY OF THE INVENTION

The principles of the present invention are premised upon the positioning of a suspended mesh of nonreactive material over the gate-membrane system, which anchors the membrane to the insulator, but through which the membrane reacts with ambient materials in substantially unimpeded fashion. In accordance with more particular aspects of the present invention, such a suspended mesh is built onto the device chip prior to application or formation of the membrane, and hence serves as a mechanism for the very formation of the membrane, as well as a superstructure to contain and anchor the membrane during the useful life of the device.

In a preferred form of the principles of the present invention, a chemfet device has a mesh grid of polyimide suspended above the gate insulator region of the device, supported by attachments about the periphery of the gate insulator area. Polymeric membrane material, in liquid form, may thus be deposited onto the mesh, thereby to wick into the void between the mesh and the insulator, with the balance to be cured over the mesh, or evaporated away. Upon suitable curing of the membrane, the mesh forms a support anchor and enclosure for the membrane.

In a preferred method of producing such devices, the formation of the grid is interposed as a series of processing steps during the basic device fabrication, preferably a wafer at a time. In particular, during the wafer processing, at the time at which aluminum bonding pads are deposited onto the chips, so also is an aluminum coating deposited over the insulated gate area of the device. The gate-insulator-aluminum area, and at least a boundary thereabout, is coated with polyimide, and thereupon, utilizing photoresist etching techniques, a gridwork of openings is formed through the polyimide, down to the aluminum. Next, again utilizing photoresist-etching techniques, the aluminum beneath the polyimide is etched away, leaving a polyimide mesh suspended above the gate insulator, supported at the region surrounding the gate area. The void formed between the polyimide mesh and the gate insulator therebeneath forms the locus of the active membrane, which in operation will react with surrounding ambient materials through the openings in the polyimide grid mesh.

It will be appreciated, therefore, that in accordance with the principles of the present invention, more or less standard integrated circuit processing steps and materials are utilized synergistically, with a relative minimum of additional processing steps, to produce a chemfet device which largely avoids the problems conventionally attendant to membrane disassociation and consequent functional and electrical degredation and failure. Moreover, utilization of polyimide as the mesh provides an excellent biocompatible interface, allowing for efficient use of the devices in the close tolerance, very demanding environment of biomedical applications.

DETAILED DESCRIPTION AND BEST MODE

Figure 1:
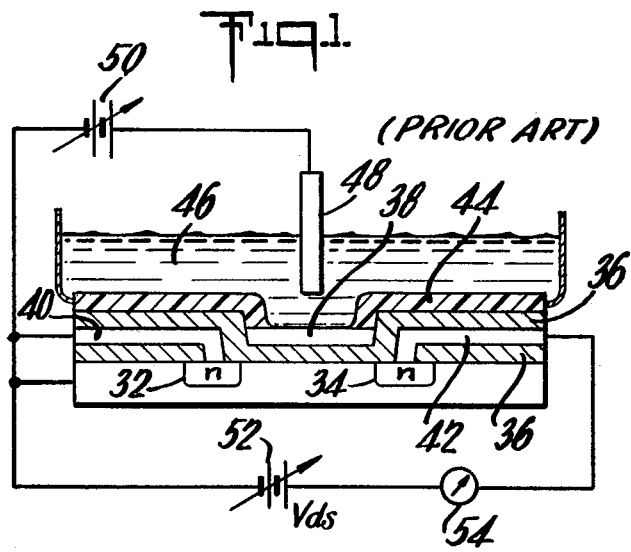
FIG. 1 shows a cross-section of a prior art chemfet device.

Referring first to FIG. 1, there is shown a prior art depiction of a chemfet style device. In particular, the FIG. 1 device represents FIG. 2 of the previously cited U.S. Pat. No. 4,020,830 to Johnson, et al. In FIG. 1, a substrate 30 has diffused therein regions 32 and 34 which define the source and drain regions of the device. Layers of insulator 36 protect the device from ambient conditions, and conductor paths 40, 42 provided for electrical connection of the drain and source electrodes 32 and 34 to external circuitry. A membrane 38 overlays the gate region between the source and drain 32 and 34, and is held in place by a solution impervious layer 44. The solution or ambient substance 46 is in contact with the membrane 38, and a reference electrode 48, suitably biased with respect to the other terminals by circuitry 50 and 52, develops the desired reference voltage in order to enable operation of the device.

Figure 2:
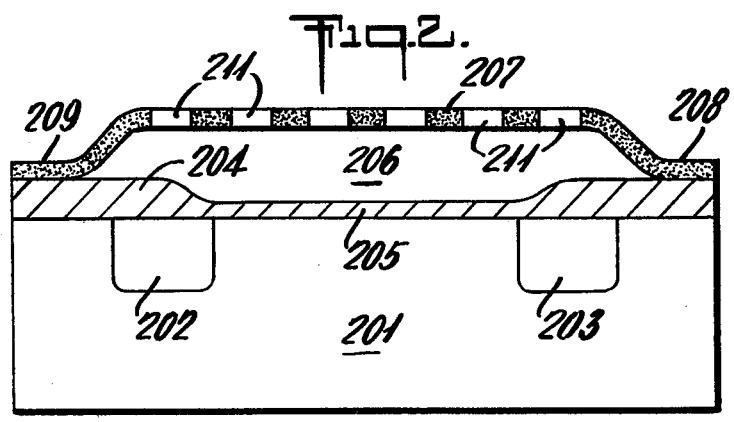
FIG. 2 shows an illustrative embodiment of the principles of the present invention.

With reference next to FIG. 2, there is shown an illustrative embodiment of the principles of the present invention, wherein a polyimide grid mesh 207 is applied over the gate area of the device. In particular, in FIG. 2, a substrate 201 has diffused therein respective drain and source regions 202 and 203. It will be appreciated that in the embodiment of FIG. 2, the actual electrical interconnection of the drain and source electrodes to the exterior (i.e. the symbolic connections 40, 42 of FIG. 1) are not shown, it being understood that in the actual pattern of the device (e.g. as discussed herein in conjunction with FIGS. 4A and 4B) will be considerably more elaborate than shown in FIG. 2. In any event, in FIG. 2, an insulator layer 204 is deposited, and intermediate the drain and source 202 and 203, forms a gate or channel region 205, the conductivity of which is to be modulated by the interaction of an overlying chemically selective membrane with ambient materials. The area 206 directly above the gate insulator region 205 is the location for application of a membrane, but in accordance with the principles of the present invention, as distinct from the prior art exemplified in FIG. 1, it is desirable first to fabricate a suspended grid mesh 207, above the gate insulator region 205, forming the void 206 into which the membrane is later formed. As noted in FIG. 2, the suspended mesh 207 is coupled to the device, and more particularly to the insulator layer 204, about the periphery of the gate insulator region, for example as shown at 208 and 209. The suspended mesh 207 defines openings 211 therethrough, through which the membrane to be located at 206 will interact with the ambient materials in selective fashion.

A preferred method of fabricating devices of the sort shown in FIG. 2 is as follows, it being understood that incorporation of the principles of the present invention is quite compatible with fabrication of more conventional type chemfet devices, entailing the addition of some intermediate process steps, the character of which are synergistic with, and at times partially overlapping with the conventional processing steps. It is to be further understood that the most advantageous time of incorporating the principles of the present invention is in the fabrication of an entire wafer of devices, although for illustrative purposes, the drawings in discussion herein relate only to a single device.

After the device is completed through application of the insulating layer 204 and 205 of the devices, aluminum is deposited over the entire wafer, for example by vacuum deposition. At this point, conventional processes call for the etching of all aluminum from the wafer except at the bonding pads and, if any, the conduction paths. In accordance with the principles of the present invention, however, the etching-photoresist masks are arranged to maintain a coating of aluminum (e.g. one micron thick) over the gate area 205 of each chip.

Next, conventional fabrication techniques would call for application of an impervious layer (e.g. 44 in FIG. 1). In a preferred embodiment of the present invention, a layer of polyimide is spun over the device, for example to a thickness of 1,000 angstroms. The polyimide layer is set, for example by pre-baking, and a photoresist masking process exposes scribe lines and bonding pads, as in the case of the more conventional procedures, and also a gridwork or mesh of spots (211 in FIG. 2) atop the aluminum pad which at this point still covers the gate insulator area.

Thereupon, utilizing conventional photoresist techniques, the polyimide is etched away over the bonding pads, from the scribe lines, and, most importantly from the standpoint of the principles of the present invention, from the gridwork of holes 211 over the aluminum-gate insulator layer. As desired, the polyimide is then rinsed and subjected to post-baking, to promote setting.

In accordance with the principles of the present invention, the aluminum layer under the recently formed mesh is to be etched away, and accordingly photoresist is deposited over the aluminum bonding pads to prevent them from also being etched away. Thereupon, the aluminum from underneath the polyimide mesh is etched away completely (for example utilizing a solution of acetic acid, nitric acid, and phosphoric acid), until there is defined the void area 206 shown in FIG. 2 between the now suspended mesh 207 and gate insulator area 205 therebeneath.

The photoresist is removed from the bonding pads, the device is suitably dried and cleaned, and at this point conventional processing of the wafer, as desired, is continued.

With reference to FIG. 2, there is shown a representation of a preferred form of a suspended mesh structure 207, with the openings 211 having been formed therein. In a preferred embodiment, the mesh 207 is suspended approximately one micron above the gate insulator. The openings are in the range of ten microns long and ten microns wide, and separated in respective dimensions by comparable amounts. As the device is first fabricated, the void 206 is filled only by air. In order to form a membrane in the void, one may simply place a drop of the membrane material in liquid form (e.g. polymeric material deposited utilizing a syringe), which wicks through the openings 211 in the suspended mesh, fills the void 206, and upon curing forms the membrane. In one embodiment, the excess liquid is evaporated off. In another, the membrane is formed over as well as under the mesh.

Figure 4A:
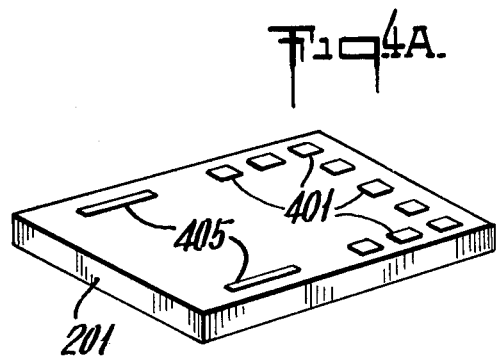
FIG. 4A shows a symbolic version of a two-device chemfet chip.
Figure 4B:
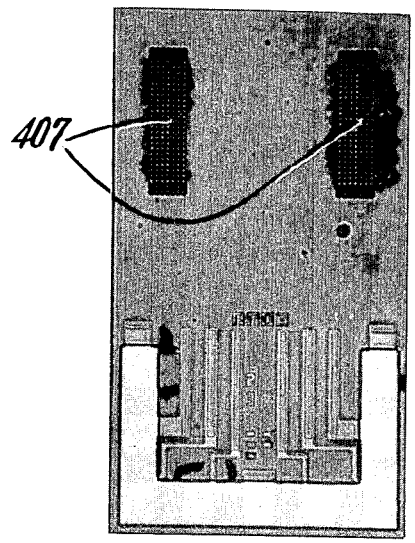
FIG. 4B shows a top view of such a chip incorporating the principles of the present invention.
Figure 3:
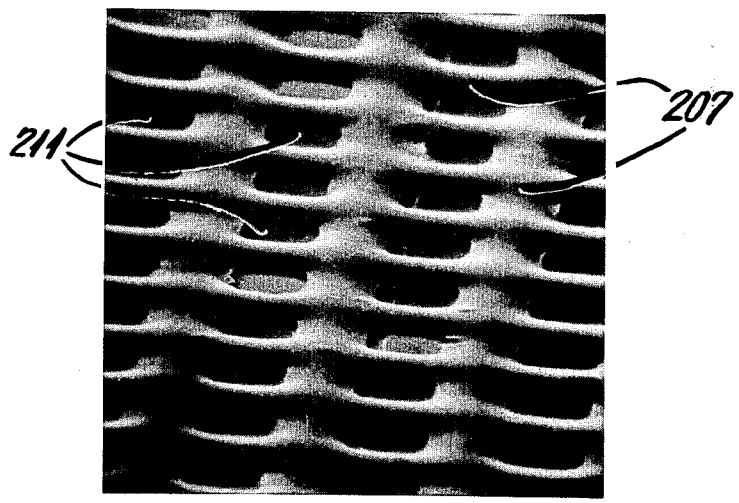
FIG. 3 shows a suspended mesh gate membrane anchor in accordance with the principles of the present invention.

Referring finally to FIGS. 4A and 4B, there is shown somewhat symbolically the application of the principles of the present invention to a two device chip. In particular, the chip 201 of FIG. 4A represents a sort of semiconductor chip which is known to be practicable, each chip 201 including two separate chemfet devices. The bonding pads 401 to the chip are shown spaced away from the gate insulator areas 405 of the respective devices. As noted in FIG. 4B, respective polyimide suspended meshes 407 are disposed over the completed chip, with the balance of the devices clustered at the opposite end thereof.

It will be appreciated that the foregoing sets forth preferred and illustrative embodiments of the principles of the present invention, but that numerous alternative embodiments will occur to those of ordinary skill in the art, without departure from the spirit or scope of the present invention. For example, it is not contemplated that the principles of the present invention are limited to a specific composition of the suspended mesh (other polymers or other materials may be substituted for the polyimide) nor specific dimensions. The fabrication processing steps set forth are in large respect characteristic of the state of the art of semiconductor fabrication, but the specific aspects of photoresist-etching, and curing as well as selection of materials, will no doubt advance with time, and it is to be anticipated that the principles of the present invention may be applied even with greater facility to the newer processing techniques. Finally, it is to be anticipated that devices which employ different overall forms, such as different junction configurations between input and output (e.g. single or multiple junction devices) will be perfectly amenable to application of the principles of the present invention, to the extent that such devices employ a gate style membrane of the short discussed herein.

I claim:

1. A method for fabricating selectively responsive field effect devices whose electrical charcteristics are responsive to a given substance, comprising the steps of:
   (a) providing at least one of said devices including an insulated gate region;
   (b) covering at least said gate region with a first material;
   (c) covering at least said first material with a second material, said second material being coupled to said device at least at predetermined points about the periphery of said gate region;
   (d) selectively forming openings through said second material to form a grid pattern;
   (e) selectively removing said first material from beneath said second material in said gate region; and
   (f) applying membrane material through said grid openings to fill at least the void between said gate region and said second material;
   (g) whereby said ambient substances may react with said device through direct exposure to said membrane, whilst said grid protects and anchors said membrane.

2. A method as described in claim 1 wherein said first material is aluminum, and said step of selectively removing said first material comprises etching said aluminum away, substantially completely, using an acid etchant solution.

3. A method as described in claim 1 wherein said second material is polyimide, and wherein said step of selectively forming openings comprises the steps of developing a gridwork pattern of photoresist over said second material, and etching the openings in said polyimide through to said first material.

* * * * *